United States Patent [19]
Shapiro

[11] Patent Number: 5,493,124
[45] Date of Patent: Feb. 20, 1996

[54] APPARATUS FOR MEASURING RADIATION TRANSMITTANCE OF A PROCESS FLUID

[75] Inventor: Arthur J. Shapiro, Maidens, Va.

[73] Assignee: Infilco Degremont, Inc., Richmond, Va.

[21] Appl. No.: 234,650

[22] Filed: Apr. 28, 1994

[51] Int. Cl.⁶ .................................................. G01N 21/33
[52] U.S. Cl. ...................................... 250/373; 250/432 R
[58] Field of Search ................................ 250/373, 431, 250/431 R, 435, 301

[56] References Cited

U.S. PATENT DOCUMENTS

| | | | |
|---|---|---|---|
| 2,206,922 | 7/1940 | Smith | 250/301 |
| 2,959,677 | 11/1960 | Robinson et al. | 250/373 |
| 3,462,597 | 8/1969 | Young. | |
| 3,566,105 | 2/1971 | Wiltrout et al. | 250/435 |
| 4,103,167 | 7/1978 | Ellner | 250/373 |
| 4,304,996 | 12/1981 | Blades | 250/373 |
| 4,358,204 | 11/1982 | Ellner | 366/118 |
| 4,367,410 | 1/1983 | Wood | 250/431 |
| 4,434,364 | 2/1984 | Correa et al. | 250/301 |
| 4,899,056 | 2/1990 | Ellner | 250/431 |
| 5,281,823 | 1/1994 | Weltz et al. | 250/372 |
| 5,302,822 | 4/1994 | Weltz et al. | 250/431 |

Primary Examiner—Carolyn E. Fields
Attorney, Agent, or Firm—Miller & Christenbury

[57] ABSTRACT

Apparatus for measuring intensity of UV radiation transmittance through a process fluid including a radiation source, a UV detector and a canopy positioned to extend over a space formed along a distance separating the radiation detector and the radiation source located in the fluid, the canopy having an opening for flow of process fluid into and out of the canopy.

20 Claims, 10 Drawing Sheets

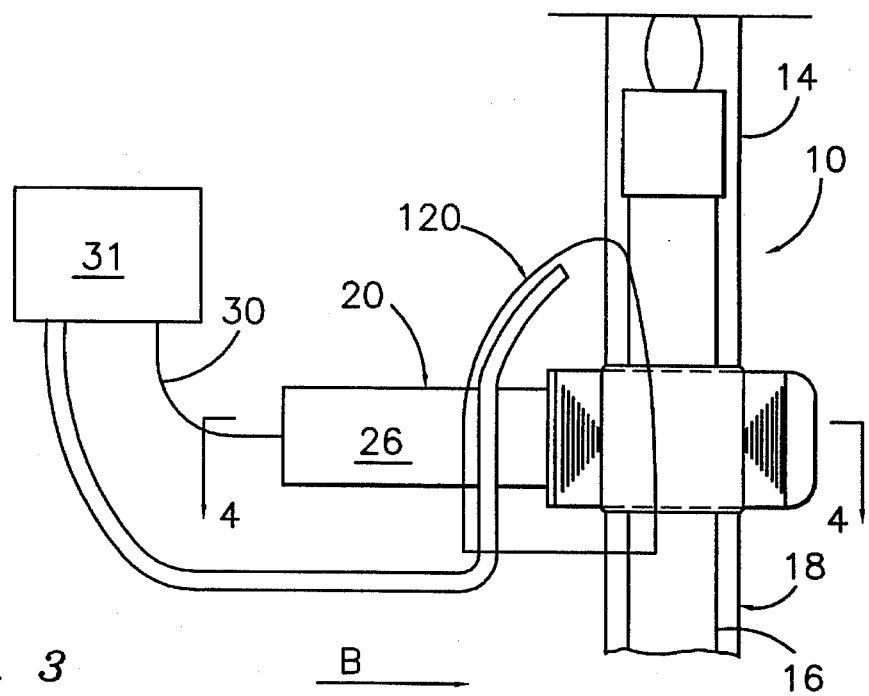
Fig. 3
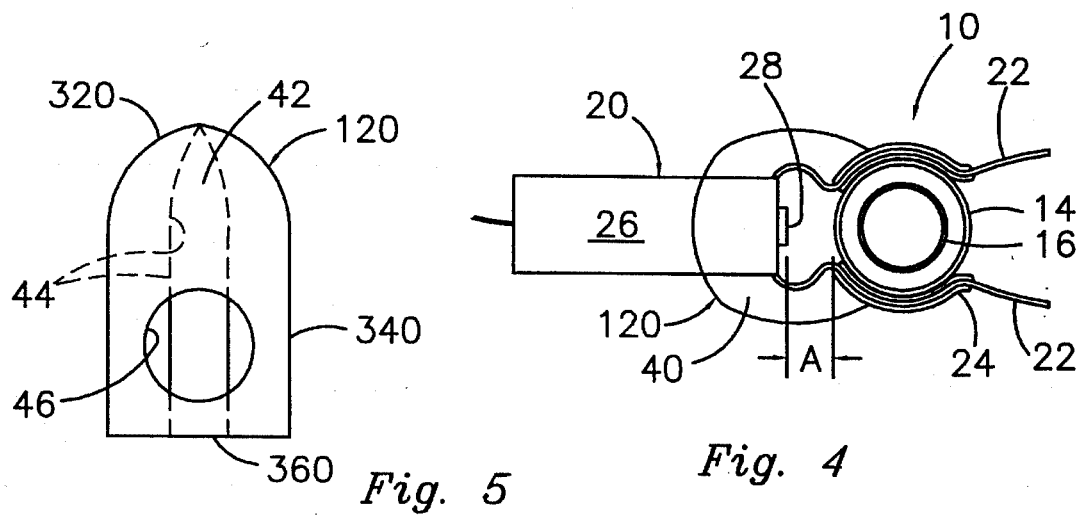
Fig. 5
Fig. 4
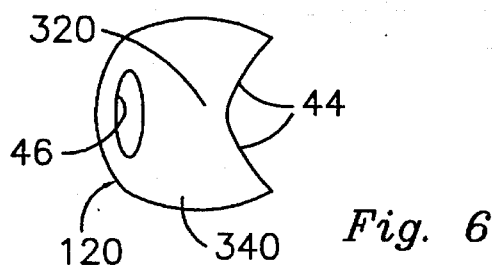
Fig. 6

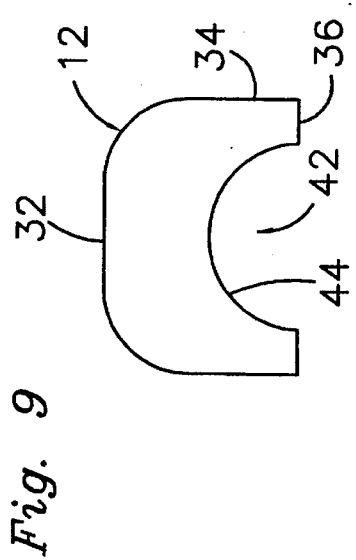
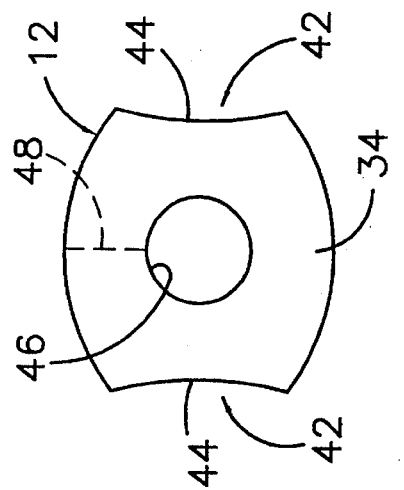
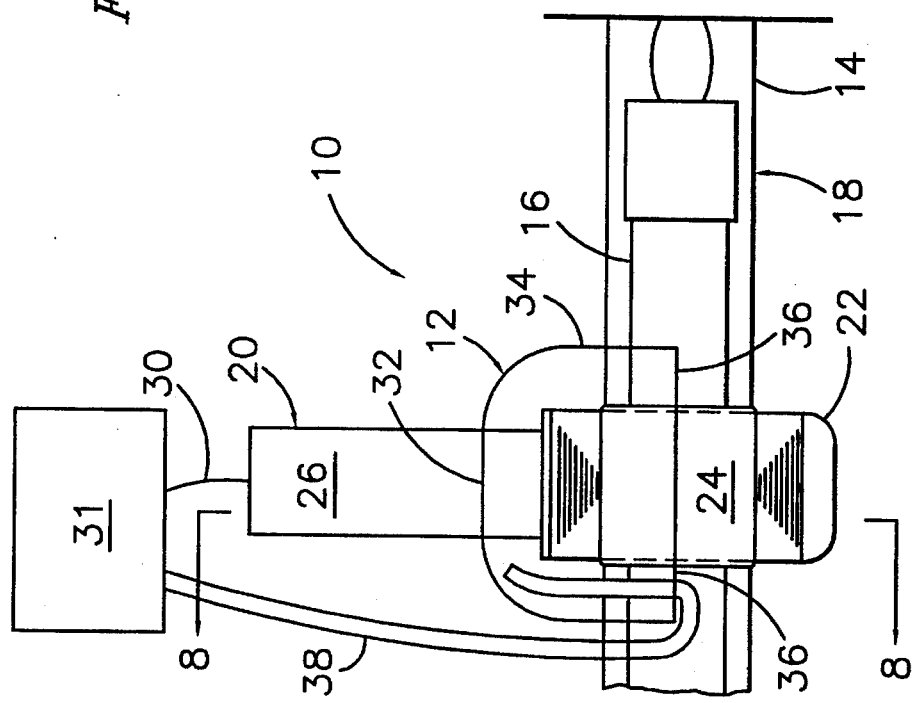
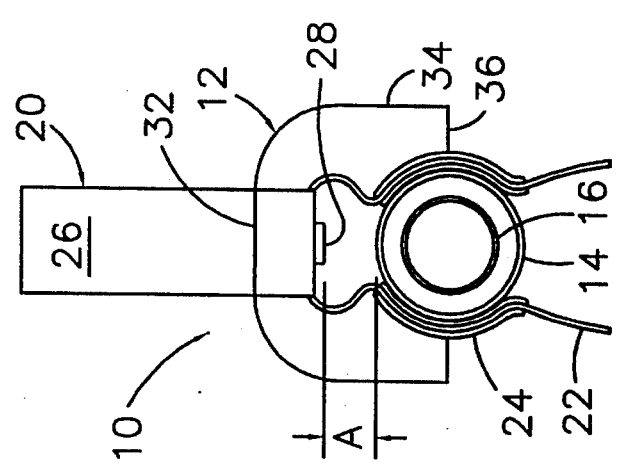
Fig. 9
Fig. 10
Fig. 7
Fig. 8

APPARATUS FOR MEASURING RADIATION TRANSMITTANCE OF A PROCESS FLUID

BACKGROUND OF THE INVENTION

The present invention relates to radiation transmittance of fluids, particularly to measuring the transmission of ultraviolet radiation through water.

FIELD OF THE INVENTION

Systems and apparatus for disinfection of water with ultraviolet light have rapidly developed in view of increased environmental awareness, the accompanying regulations associated with disposal and treatment of waste and potable water and the desire to avoid or reduce reliance on chemical treatment. This growing need has resulted in a similar requirement for producing more efficient and reliable ultraviolet disinfection systems for effectively and safely treating waste and potable water over prior art systems. Regulations associated with such systems, methodology and apparatus developed to disinfect water with ultraviolet light have become increasingly stringent in an effort to provide increases in reliability to ensure proper system capabilities, operation and maintenance.

Many process fluids contain highly dangerous and toxic contaminants and, in cases where ultraviolet disinfection is appropriate, contain potentially harmful microorganisms which are or can be hazardous to human health. It is, therefore, essential in ultraviolet disinfection systems that the systems be capable of continuously and efficiently operating over long periods of time to maintain required minimal radiation dosages applied to the process fluids as they pass through the disinfection system. Even the smallest defects in such systems, such as lamp outages, radiation dose reduction due to aged lamps or particulate and film buildup on quartz lamp sleeves and the like, can cause reduced radiation dosages, which can result in the failure to apply the appropriate intensity of ultraviolet radiation within the limited retention time to microorganisms in the process fluid. Of course, the human health hazards associated with failure to ensure complete disinfection can have grave consequences in some instances, including illness or death.

A wide variety of ultraviolet apparatus has been developed to overcome many of these problems and many regulatory agencies now require a growing number of safety features to ensure proper disinfection. For example, typical ultraviolet disinfection systems contain one or more strategically located ultraviolet sensors which measure the quantity of radiation emitted by ultraviolet lamps and transmitted through protective quartz sleeves and the process fluid. System operators can thereby intermittently or continuously measure the equivalent dosage of ultraviolet radiation applied to the process fluid. However, there have been a number of drawbacks associated with current sensor systems. For example, such systems do not properly differentiate between the effect of age of the ultraviolet lamps, wherein increasing age of the lamps results in decreased emittence of useful ultraviolet radiation; reduced dosage caused by deposits on protective lamp jackets; or changes in process liquid that may affect ultraviolet transmittance valves. Such decreases in intensity occur gradually and if not closely monitored and identified can occur without being noticed and result in costly or inappropriate maintenance and inadequate dosage applied to the process fluid.

As noted, ultraviolet intensity received by a sensor is influenced by the UV transmittance of the process fluids between the lamp and the detection end of the UV sensor. Many process fluids contain a wide variety of particulate or solid matter, colloidal or dispersed materials and dissolved compounds that absorb UV wavelength energy, together with microorganisms and the like. This reduces the ability of germicidal wavelength ultraviolet radiation to transmit through the fluid and can result in an inadequate ultraviolet radiation dose depending on the degree of transmittance. Also, the presence of such particulate matter, film forming contaminants and the like results in a coating deposited not only on the outer surfaces of the lamp protective sleeve, but on the detection end of sensors. Of course, changes in treatment process, the buildup of coatings and/or films and particulate matter over the lamp's protective quartz sleeves reduces the ability of ultraviolet radiation to be emitted into the fluid. Similarly, coatings on the sensor itself degrade its ability to detect the actual quantity of ultraviolet radiation being transmittal through the fluid due to the transmitting dampening effect of the coating film. The result of these problems is that it is difficult to precisely determine the true intensity of the ultraviolet radiation reaching the process fluid or the specific cause of reduction to UV intensity.

Depending on the characteristics of the process fluid and the quantity of particulate matter and contaminants in the fluid, film and coating buildup becomes more of a problem. A variety of lamp orientations, cleaning systems and methodologies have been developed with varying degrees of success. Typical cleaning systems address the task of cleaning outer jackets surrounding ultraviolet lights without particular attention being paid to the sensors or the area of the jackets to which the sensors are attached. Thus, it is typical for many cleaning systems to provide inadequate cleaning of the sensor and/or the area of the lamp directly adjacent the photocell without manual effort to access these remotely mounted sensors.

OBJECTS OF THE INVENTION

It is an object of the present invention to provide an apparatus capable of accurately measuring the intensity of radiation transmission to the process fluid and preferably to measure radiation transmittance substantially during real time.

It is another object of the invention to achieve the accurate measurement of radiation transmittance with a means capable of remaining within the process fluid, without the need for periodic removal from the process fluid for cleaning.

It is a further object of the invention to provide an apparatus capable of cleaning, in situ, a radiation detector and an adjacent portion of a radiation source.

It is still another object of the invention to provide an apparatus that enables one to determine the cause of reduced UV intensity during real time.

Other objects and advantages will become apparent to those skilled in the art from the drawings, the detailed description of preferred embodiments, and the appended claims.

SUMMARY OF THE INVENTION

The invention includes a system for determining the specific causes for reduction of radiation transmittance of a process fluid wherein an ultraviolet radiation source is positioned in the fluid adjacent an ultraviolet sensitive photocell also positioned in the fluid. An ultraviolet resistant cover connects to the radiation source and extends over a space extending between the detector end portion and the radiation source. The cover has an opening to permit ingress and egress of process water from the cover. An air source introduces air interiorly of the cover and simultaneously displaces at least a portion of the water from the cover.

BRIEF DESCRIPTION OF THE DRAWINGS

FIG. 3 shows another embodiment of a canopy of the invention attached to the photocell and a vertically oriented ultraviolet lamp.

FIG. 4 shows the apparatus of FIG. 3 taken along the lines and arrows 4—4 of FIG. 3.

FIG. 5 shows a side view of the canopy shown in FIG. 3.

FIG. 6 shows a top view of the canopy shown in FIG. 3.

FIG. 7 shows a photocell clamped to a horizontally oriented ultraviolet lamp and having another embodiment of a canopy in accordance with the invention.

FIG. 8 shows the apparatus of FIG. 7 taken along the lines 8—8 of FIG. 7.

FIG. 9 shows a side view of the canopy shown in FIG. 8.

FIG. 10 shows a top view of the canopy shown in FIG. 7.

DETAILED DESCRIPTION OF THE INVENTION

Figure 1:
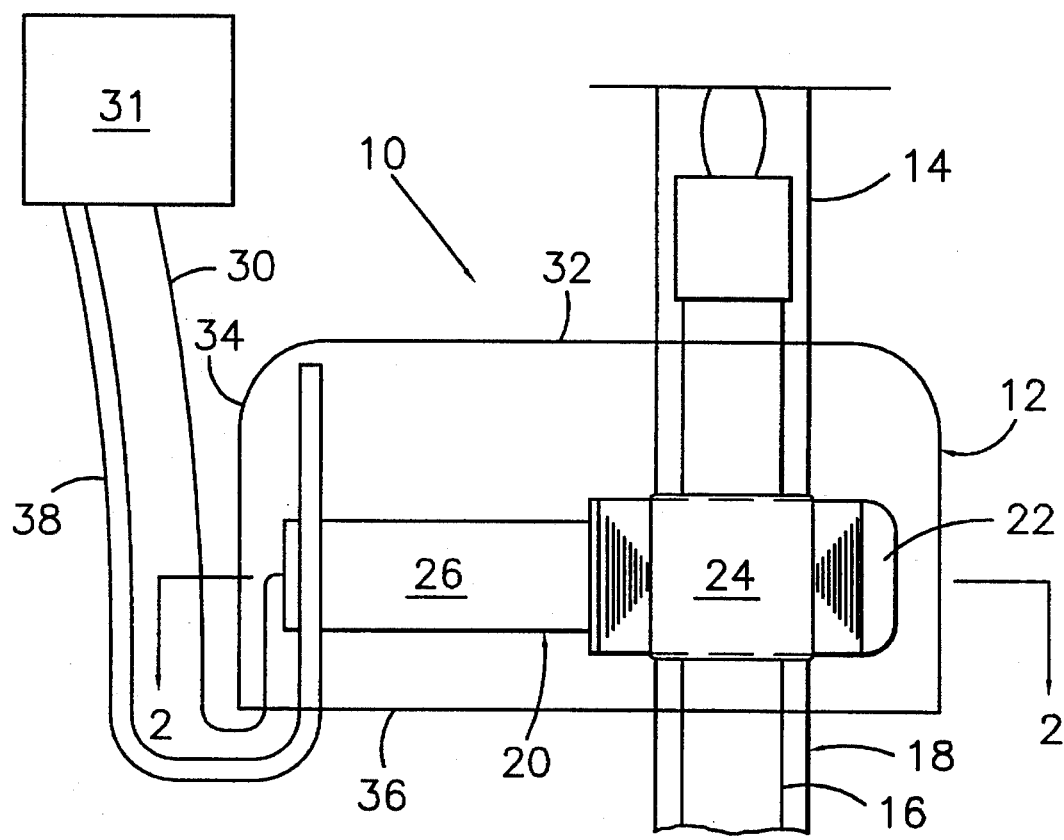
FIG. 1 shows a schematic front elevational view of a photocell attached to a vertically oriented ultraviolet lamp and having a canopy extending over the photocell in accordance with aspects of the invention.

It will be appreciated that the following description is intended to refer to the specific embodiments of the invention selected for illustration in the drawings and is not intended to define or limit the invention other than in the appended claims. Turning now to the specific forms of the invention as illustrated in the drawings and referring particularly to FIGS. 1 and 2, the number "10" designates a system for measuring intensity of radiation transmittance through a process fluid. System 10 includes a canopy 12 connected to an outer jacket 14 having an ultraviolet light 16 located concentrically interiorly of outer jacket 14. Together, outer jacket 14 and ultraviolet light 16 comprise a lamp 18.

A radiation detector 20 is mounted onto outer jacket 14 of lamp 18. Detector 20 includes a pair of clamping arms 22. Each clamping arm 22 has a soft, flexible sleeve 24 which engages the outer surface of outer jacket 14 of lamp 18. Clamping arms 22 connect to a housing 26 in which photocell 28 is located. Radiation detector 20 connects to control, air supply and display apparatus 31 by wire 30.

Figure 2:
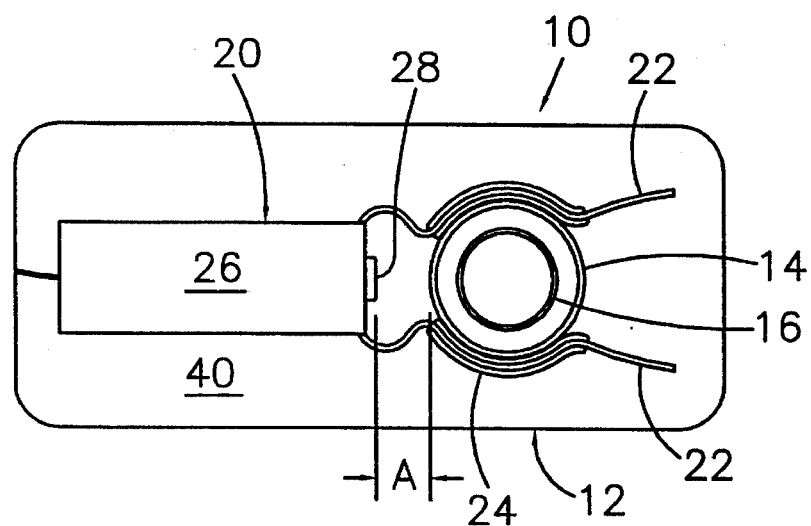
FIG. 2 shows the apparatus of FIG. 1 taken along the lines and arrows 2—2.

Canopy 12 generally includes a ceiling 32, sidewall 34 and lower opening 36. As shown in FIGS. 1 and 2, canopy 12 extends over a portion of lamp 18 and covers radiation detector 20 in its entirety. Air supply tube 38 extends through opening 36 and into an interior space 40 defined by ceiling 32, walls 34 and opening 36 on one end and connects to controller 31.

Clamping arms 22 and housing 26 are configured to accurately position the detection end of photocell 28 a prescribed distance from outer jacket 14 of lamp 18, the distance shown by arrow A in FIG. 2. The distance along arrow A defines a "measuring space" into and through which process fluid flows.

FIGS. 3–6 show another embodiment of canopy 12 applied to a substantially vertically oriented lamp. The canopy of FIGS. 3–6 is labelled "120" for convenience. Canopy 120, as particularly shown in FIG. 5, includes a side wall 340 which has an outer jacket engaging slot 42. Slot 42 is defined by a pair of sealing edges 44 which extend between ceiling 320 and lower opening 360. Sealing edges 44 sealingly engage the outer surface of outer jacket 14 of lamp 18 as particularly shown in FIG. 4.

Canopy 120 is held into sealing engagement with lamp 18 by a friction fitting of housing 26 and mounting opening 46 of canopy 120. Such a friction fitting is a substantially water-tight fitting and is formed by the diameter of mounting opening 46 being slightly smaller than the diameter of housing 26. Thus, movement of radiation detector 20 in the direction shown by arrow B in FIG. 3 into a clamped position on lamp 18 causes canopy 120 to similarly move in the direction shown by arrow B and sealing edges 44 sealingly engage the outer surface of outer jacket 14. The friction fit of housing 26 and mounting opening 46 causes sealing engagement of canopy 120 with radiation detector 20 and permits application of sealing force by sealing edges 44 against outer jacket 14. Canopy 120 is sized to completely cover the distance and the "measuring space" between outer jacket 14 and the detection end of photocell 28 shown by arrow A in FIG. 4.

FIGS. 7–10 show yet another embodiment of canopy 12, canopy 12 being applied to a substantially horizontally oriented lamp 18. Radiation detector 20 is clamped into a desired position on lamp 18 in the same manner as shown in the previous figures. Canopy 12 is friction mounted onto housing 26 in the same manner as described for the embodiment shown in FIGS. 3–6, namely mounting opening 46 as shown in FIG. 10. Mounting opening 46 sealingly engages the outer surface of housing 26 by virtue of housing 26 having a slightly larger diameter than the diameter of mounting opening 46. Canopy 12 further includes sealing edges 44 which form a pair of slots 42 that engage outer jacket 14.

FIG. 10 depicts an optional feature of canopy 12 (the optional feature being applicable to all embodiments of the invention, which is shown by the dashed line). The dashed line represents a cut 48 extending along wall 34 of canopy 12. This permits ease of attachment and removal of canopy 12 from radiation detector 20 without disturbing its wire connection 30 or its clamping position on lamp 18. Cut 48 can further include, if desired, means to assist in maintaining a seal between respective edges forming cut 48. Such means can include an overlapping feature, an additional flap covering cut 48, adhesive material, fasteners and the like, all of which are not shown but are well known in the art.

Figure 11:
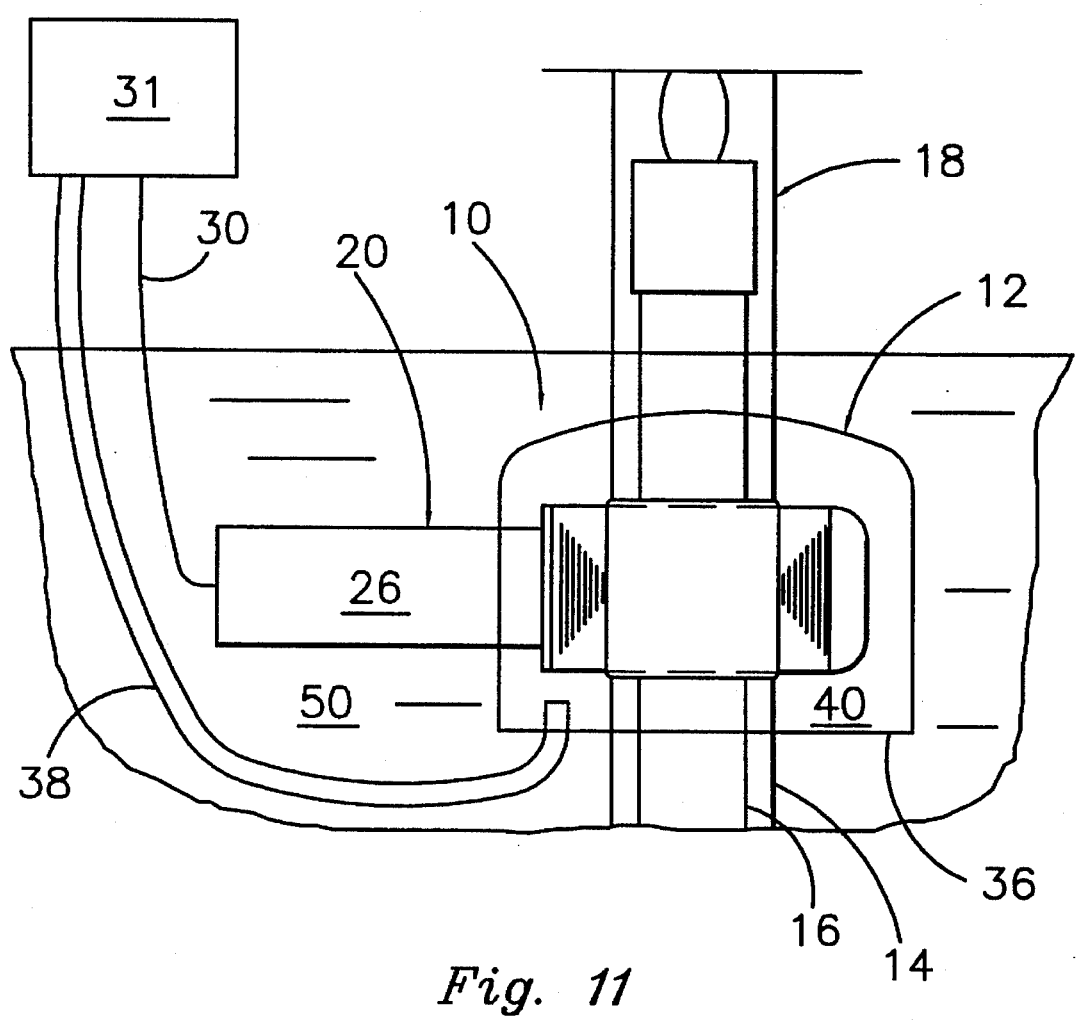
FIG. 11 shows a front elevational schematic view of another embodiment of a canopy in accordance with the invention in conjunction with a photocell and a substantially vertically oriented ultraviolet lamp, all positioned within a process fluid.
Figure 12:
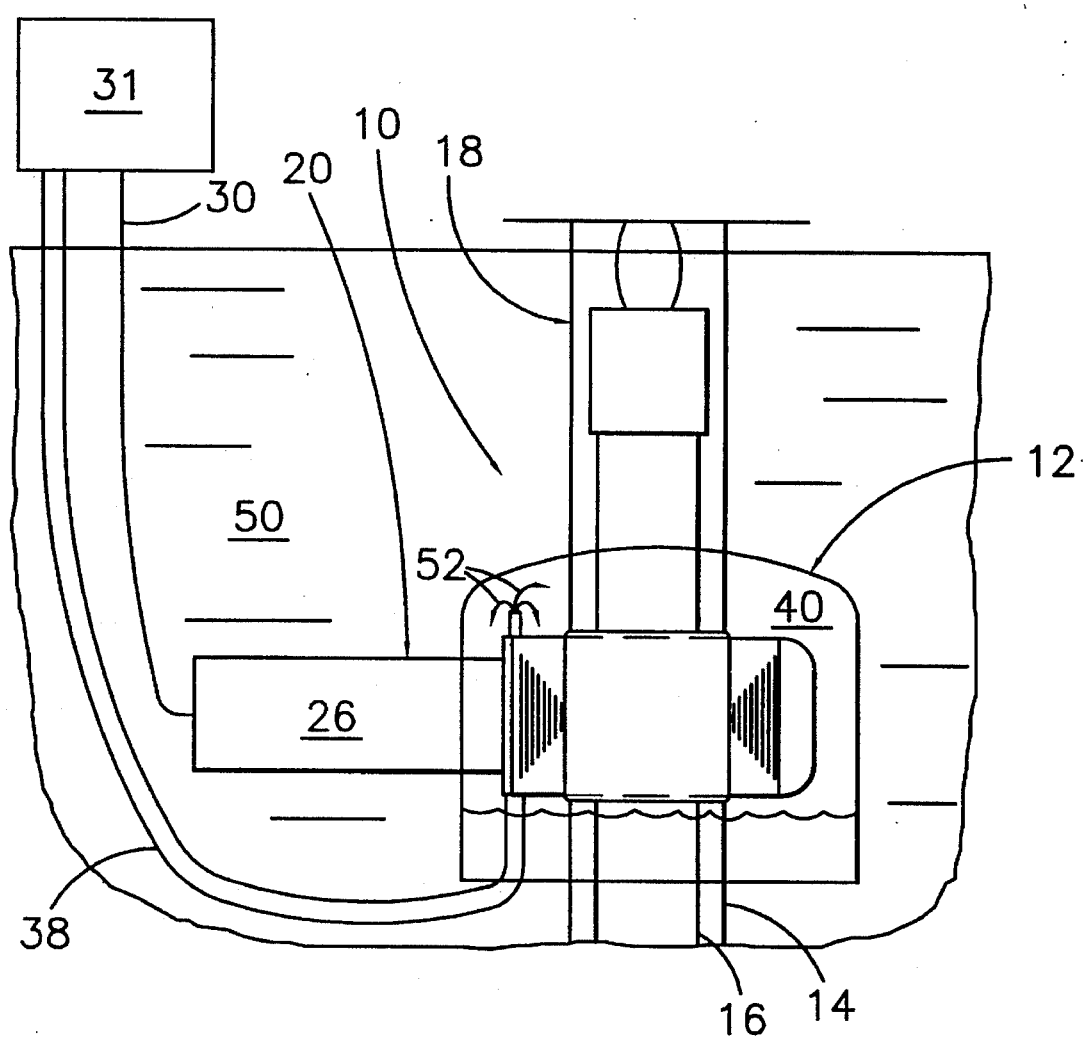
FIG. 12 shows the apparatus shown in FIG. 11 in the process fluid of FIG. 11 with the process fluid having been forced from underneath the canopy by injection of air.

FIGS. 11 and 12 show operational aspects of system 10. In particular, system 10 is submerged within a body of process fluid 50. Process fluid 50 may be of the type to be treated with any number of disinfection apparatus known in the art and in disinfection systems such as open or closed channels, tanks and the like. Process fluid 50 extends substantially entirely into interior space 40 of canopy 12 in FIG. 11. In FIG. 12, however, interior space 40 of canopy 12 is partially filled with process fluid 50 and partially void of process fluid 50 as a result of introduction of air through air supply tube 38, the supply of air being represented by arrows 52.

Figure 13:
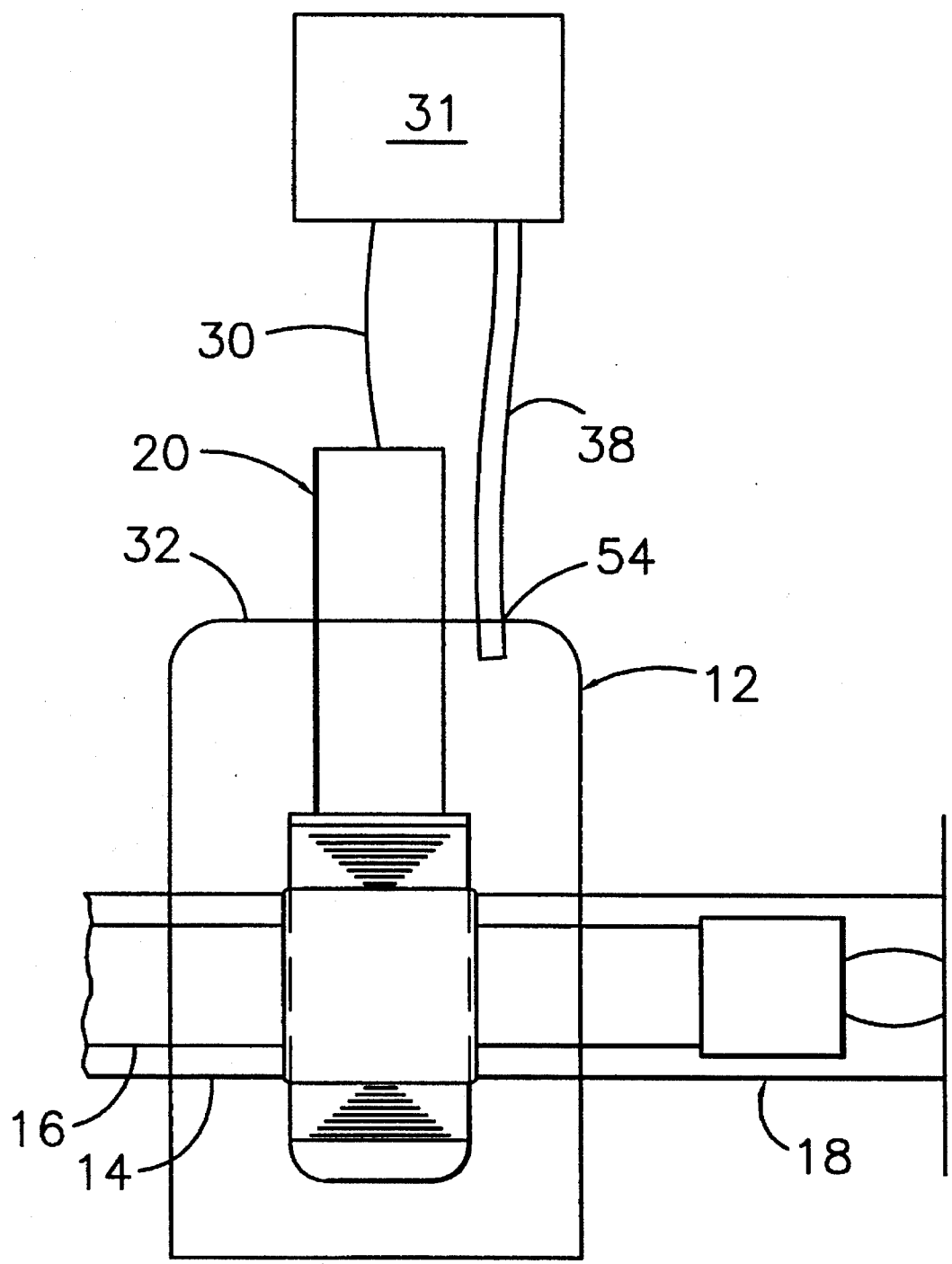
FIG. 13 shows another embodiment of a canopy in accordance with the invention extending over a photocell and a portion of a substantially horizontally oriented lamp with an air source extending through an upper portion of the canopy.

FIG. 13 shows yet another embodiment of canopy 12 wherein air supply tube 38 extends through a ceiling opening 54 in ceiling 53 of canopy 12.

Figure 14:
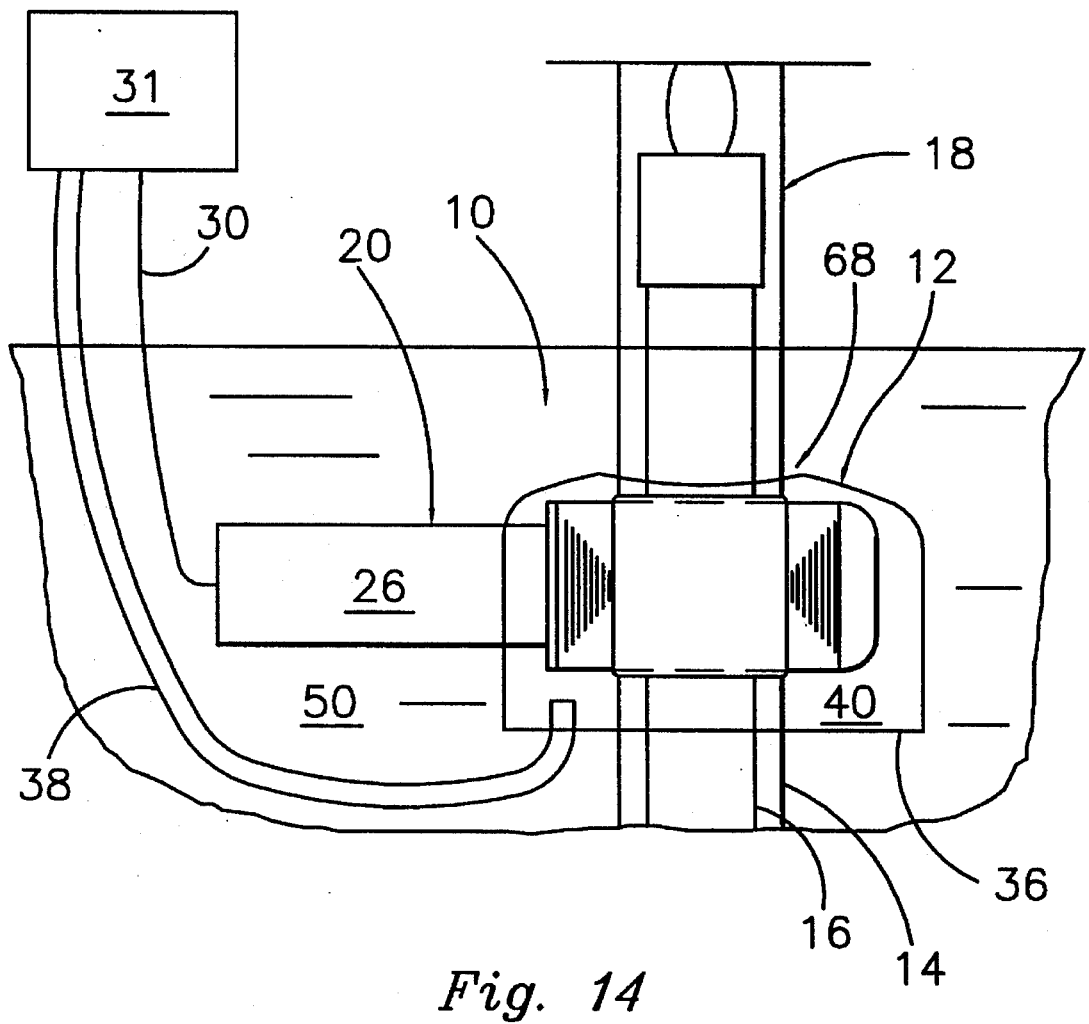
FIG. 14 shows yet another embodiment of a canopy of the invention applied to apparatus substantially as shown in FIG. 11.
Figure 15:
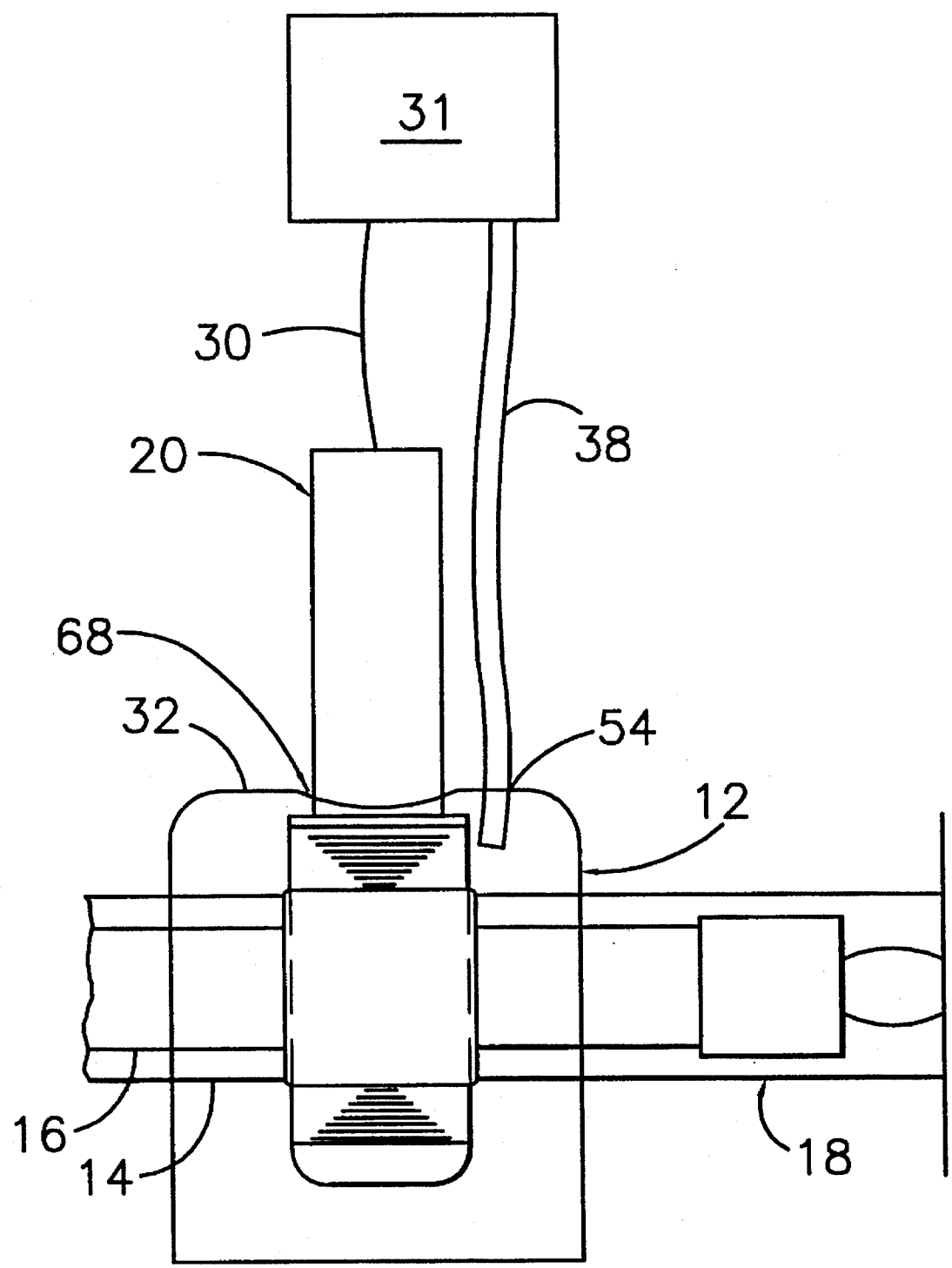
FIG. 15 shows still another embodiment of a canopy of the invention applied to apparatus substantially as shown in FIG. 13.
Figure 16:
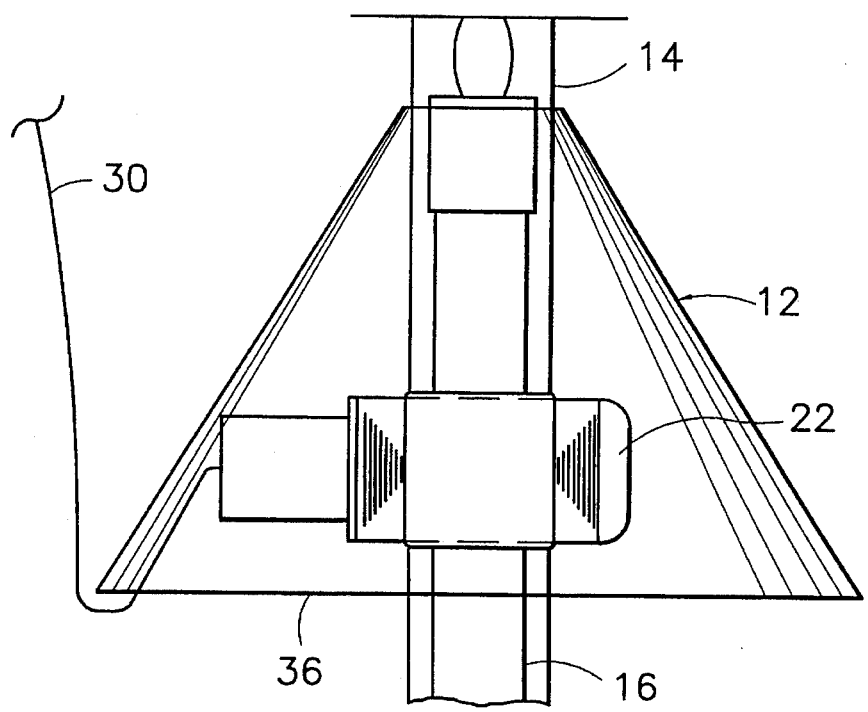
FIGS. 16–19 show additional embodiments of canopies of the invention in conical shape, cube shape, spherical shape and rectangular prism shape as applied to apparatus substantially as shown in FIG. 1.
Figure 17:
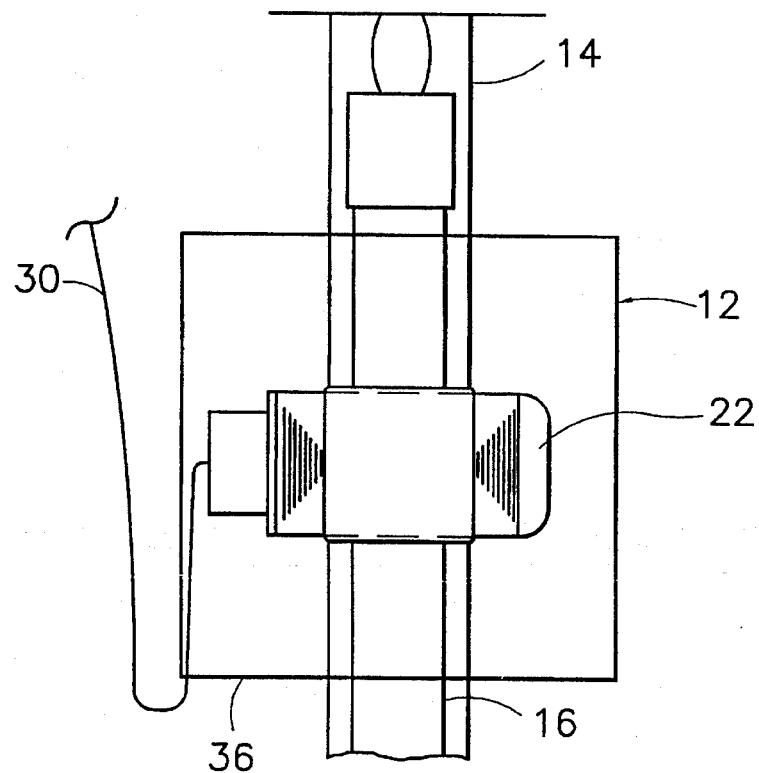
Figure 18:
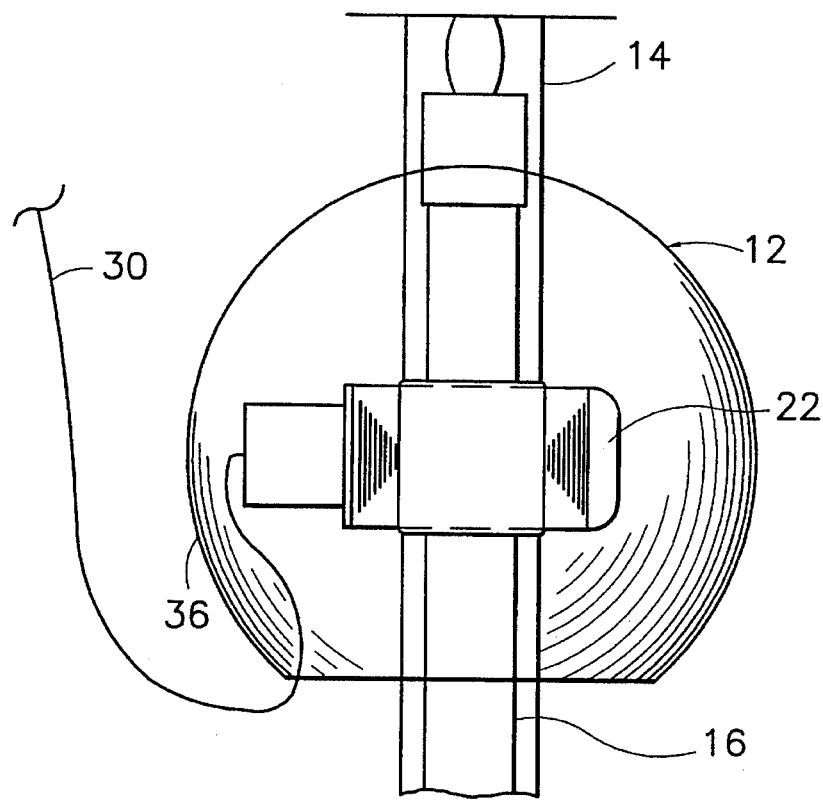
Figure 19:
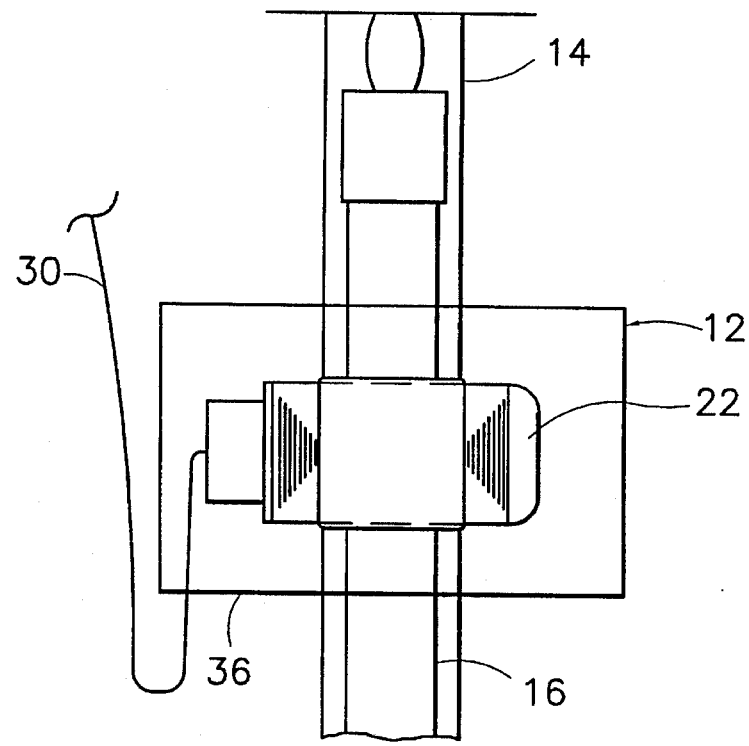

FIGS. 14 and 15 show additional preferred embodiments of the invention wherein alternate types of canopies 12 are mounted over vertically and horizontally oriented lamps 18, respectively. Unlike the canopies 12 shown in FIGS. 1–13, the canopies of FIGS. 14 and 15 are not fluid tightly sealed to lamp 18 in the case of FIG. 14 and radiation detector 20 in the case of FIG. 15. Instead, each canopy 12 has a canopy opening 68 which has a diameter larger than that of the jacket 14 in FIG. 14 and radiation detector 20 in FIG. 15. Accordingly, there is no friction fit of canopy 12 and a small gap exists through opening 68. In each case, this permits canopy 12 to simply rest on radiation detector 20 in FIG. 14 and on jacket 14 in FIG. 15. It is, however, possible to have a friction fit between canopy 12 and radiation detector 20 in FIG. 14 and between canopy 12 and jacket 14 in FIG. 15, if desired. Air supply 31 supplies air through air supply tube 38 in the same manner as previously described with respect to FIGS. 1–13.

FIGS. 16–19 show canopy 12 in five additional shapes, such as conical, cube, spherical and rectangular prism applied to jacket 14.

Operation of system 12 and its associated apparatus will now be described. Radiation detector 20 is mounted onto lamp 18 in the usual manner, which is well known in the art. Depending on the particular structure of canopy 12, canopy 12 may be mounted simultaneously with the mounting of radiation detector 20 or may be mounted either before or after such mounting of radiation detector 20 onto lamp 18. For example, in the embodiment shown in FIGS. 1 and 2, mounting of canopy 12 would typically occur subsequent to placement of radiation detector 20 on lamp 18, although it could be applied prior to mounting of radiation detector 20. In the embodiment shown in FIGS. 3–6, attachment of canopy 120 preferably occurs simultaneously with mounting of radiation detector 20 onto lamp 18 due to the friction mounting aspect of canopy 120 onto housing 26 and the sealing engagement of sealing edges 44 against outer jacket 14. The embodiment shown in FIGS. 7–10 is preferably mounted in a manner similar to that described with respect to FIGS. 3–6.

Prior to displacement of process fluid 50 from interior space 40, photocell 28 provides a normal operational ultraviolet intensity reading. When the operator of the ultraviolet disinfection system and transmittance system 10 desires to determine the intensity of UV radiation transmittance of the process fluid, which fluid extends in a normal operational state into interior space 40 substantially as shown in FIG. 11, the operator actuates a supply of air through air supply tube 38 by way of controller 31. Introduction of air into interior space 40 causes process fluid 50 to be forced outwardly of interior space 40 through opening 36 by means of simple air displacement.

Subsequent to displacement of fluid 50 from interior space 40 of canopy 12, as shown in FIG. 12, the radiation intensity reading of photocell 28 changes. In the case where air is the displacement fluid, the ultraviolet intensity reading monitored subsequent to fluid displacement typically increases because of the greater ability of air to more clearly transmit ultraviolet radiation than process fluids, especially when such process fluids contain particulate matter and the like. The difference between the initial ultraviolet intensity reading prior to fluid displacement and the intensity reading subsequent to fluid displacement provides the operator with the means to determine true transmittance of the process fluid. Proper adjustments and/or remedial measures may then be taken more effectively to ensure adequate radiation dosage application. Such measures can include jacket cleaning, UV lamp replacement, use of additional lamps, changes to upstream process and/or fluid flow rate changes and other actions, all known in the art.

When the operator determines that cleaning of photocell 28 and lamp portion around photocell 28 is warranted, such as on a periodic basis, alternate fluids may be introduced into interior space 40 by air supply tube 38. For example, a wide variety of liquid cleaning agents, such as citric acid, are well known in the art and may be periodically introduced either manually or automatically into interior space 40. Such cleaning agents at least partially displace process fluid 50, thereby permitting cleaning action of the cleaning agent against the portion of jacket 14 contained within interior space 40 and the detection end of photocell 28. Placement of supply tube 38 in a desired position can direct cleaning agent to a specifically desired point, such as directly into the "measurement space" shown by arrow A. This enhances cleaning of the surfaces through which radiation transmittance is measured. Similarly, air supply tube 38 and controller 31 can be used to vent air from interior space 40 upon concluding measurement procedures so that radiation detector 20 can resume normal operation.

The embodiments shown in FIGS. 14 and 15 operate substantially similarly to the embodiments described with respect to FIGS. 1–13, with several exceptions. In FIGS. 14 and 15, air supplied through air supply tube 38 interiorly of canopy 12 is free to escape through opening 68 due to the gap between the edge of the opening and lamp 14 in FIG. 14 and radiation detector 20 in FIG. 15. It is therefore necessary to supply air from air supply 31 at a greater rate than the rate of escape of air through opening 68. In this manner, water will be displaced from the interior space 40 of canopy 12 as previously described. In this embodiment, however, there is the additional advantage that there is no need to evacuate the air once it has been supplied in order to return water into interior space 40 of canopy 12. This occurs constantly, even during the supply of air, and permits interior space 40 to rapidly refill with process water upon terminating the supply of air.

Although this invention has been described in connection with specific forms thereof, it will be appreciated that a wide array of equivalents may be substituted for the specific elements shown and described herein without departing the spirit and scope of this invention as defined in the appended claims. For example, a wide variety of sizes and shapes of canopy 12 may be employed as an alternative to the sizes and shapes shown and described herein. Such shapes and sizes may be employed so long as canopy 12 (or 120)

ensures that the "measurement space" along arrow A is contained within interior space 40 to permit displacement of process fluid 50 from the "measurement space." It is not necessary for canopy 12 to be fully supported by either or both of lamp 18 and radiation detector 20, so long as the "measurement space" is provided. Various types of radiation detectors 20 and jacket 14/light 16 arrangements may be employed. For example, many photocells 28 are attached to lamps 18 with means other than those shown and described herein and lamps 18 may be vertically or horizontally oriented or may be oriented at angles in between. Radiation detectors (sensors) may be remotely supported separate from the lamps (and module). When the lamps (and module) are placed within the process fluid, canopy 12 and radiation detector 20 automatically are properly located or positioned for measuring. Also, many types of photocells or radiation sensitive detectors may be employed, including fiber optic sensors with integrated or remote circuitry. Further, canopy 120 may be applied to systems detecting radiation other than ultraviolet radiation, such as infrared, for example.

Although sealing engagement of canopy 12 has been couched primarily in terms of friction fit, it is possible for other means of sealing to be employed. For example, various "O" ring arrangements, adhesives, packing materials and the like may be employed. Also, a wide variety of materials may be employed for canopy 12 so long as they are radiation resistant, preferably ultraviolet radiation resistant. For example, NEOPRENE, TEFLON, silicone rubber and stainless steel may be used as materials for canopy 12. Canopy 120 is further preferably manufactured from a material that is highly flexible yet sufficiently shape retentive to resist against deformation caused by air supplied by air supply tube 38.

Moreover, although opening 36 has been depicted as a large opening relative to the size of canopy 12, it is possible for opening 36 to be highly restricted, so long as process fluid 50 is free to flow inwardly and outwardly of opening 36. It is possible to obtain air supply and cleaning agents from any number of sources. For example, one preferred manner of supplying air is from a fan mounted in the upper housing of modules in which the lamps 18 are contained. In such a case, as is possible in other cases, controller 31 does not directly control air supply in conjunction with radiation detector 20. In fact, controller 31 can encompass a wide variety of control, display and air/fluid supply devices capable of operation completely independently from each other.

What is claimed is:

1. Apparatus for measuring intensity of UV radiation transmittance through a process fluid comprising a radiation source, a UV detector and a canopy positioned to extend over a space formed along a distance separating said radiation detector and said radiation source, said canopy having an opening for flow of process fluid into and out of said canopy.

2. The apparatus defined in claim 1 further comprising a measuring fluid supply source connected to said canopy to introduce a measuring fluid interiorly of said canopy and selectively displace either all or at least a portion of said process fluid from said canopy.

3. The apparatus defined in claim 2 wherein said measuring fluid supply source is an air supply.

4. The apparatus defined in claim 1 wherein said radiation source is an ultraviolet lamp.

5. The apparatus defined in claim 1 wherein said radiation detector is an ultraviolet sensitive photocell.

6. The apparatus defined in claim 1 wherein said canopy is made from ultraviolet resistant material.

7. The apparatus defined in claim 1 wherein said canopy has an upper portion having an opening, the upper portion being substantially fluid tightly sealed to said radiation source.

8. The apparatus defined in claim 1 wherein said canopy is substantially fluid tightly sealed between said detector and said radiation source along said space.

9. The apparatus defined in claim 1 wherein said radiation source is an elongated substantially vertically oriented ultraviolet lamp.

10. The apparatus defined in claim 1 wherein said radiation source is an elongated substantially horizontally oriented ultraviolet lamp.

11. The apparatus defined in claim 1 wherein said radiation source comprises an ultraviolet lamp positioned within a fluid tight jacket.

12. Apparatus for measuring intensity of UV radiation transmittance through a process fluid comprising a source of radiation, a UV radiation detector adapted to detect radiation emitted from said source of radiation, a canopy positioned to extend over a space formed along a distance separating said radiation detector and said source of radiation, said canopy having an opening for flow of process fluid into and out of said canopy and a measuring fluid supply source connected to said canopy to introduce a measuring fluid interiorly of said canopy and displace at least a portion of said process fluid from said canopy.

13. An ultraviolet radiation sensitive detector system immersible in fluids comprising a radiation source, an ultraviolet radiation sensitive detector adapted to detect radiation emitted from said radiation source, and an ultraviolet resistant canopy having an upper portion and a lower portion having an opening, said upper portion extending over a distance between said radiation source and a detection portion of the radiation sensitive detector and forming a fluid evacuable space along said distance.

14. The system defined in claim 13 further comprising a source of test fluid connected to said upper portion.

15. The system defined in claim 13 wherein said canopy is in a shape selected from the group consisting of cone, cube, cup, spherical and rectangular prism.

16. The system defined in claim 13 wherein said radiation source is substantially vertically oriented.

17. The system defined in claim 13 wherein said radiation source is substantially horizontally oriented.

18. The system defined in claim 13 wherein said canopy is substantially fluid tightly sealed to said radiation source and said detection portion.

19. A system for determining the intensity of radiation transmittance of wastewater comprising:

an ultraviolet radiation source;

an ultraviolet sensitive photocell, said photocell comprising means for detecting the intensity of ultraviolet radiation transmitted through said wastewater, said photocell having a detector portion positioned at a distance from said radiation source sufficient to detect ultraviolet emitted from said radiation source and travelling through said wastewater;

an ultraviolet resistant canopy extending over a space extending between said detector portion and said radiation source, said canopy having an opening to permit ingress and egress of wastewater therefrom.

20. The system defined in claim 19 further comprising an air source positioned to introduce air into and selectively displace all or at least a portion of said wastewater out of said canopy.

* * * * *